United States Patent [19]

Li et al.

[11] Patent Number: 5,305,749

[45] Date of Patent: Apr. 26, 1994

[54] SIDE-LOADING OF PATIENT INTO MRI C-MAGNET WHILE MAINTAINING ADJACENT OPEN ACCESSIBILITY TO PATIENT

[75] Inventors: Andrew J. Li, South San Francisco; Leon Kaufman, San Francisco, both of Calif.

[73] Assignee: The Regents of the University of California, Oakland

[21] Appl. No.: 950,277

[22] Filed: Sep. 24, 1992

[51] Int. Cl.$^5$ .......................................... A61B 5/055
[52] U.S. Cl. ............................ 128/653.2; 128/653.5; 324/318; 5/601
[58] Field of Search ............... 128/653.1, 653.2, 653.5; 5/600, 601; 324/318, 322

[56] References Cited

U.S. PATENT DOCUMENTS

| | | | |
|---|---|---|---|
| 4,407,292 | 10/1983 | Edrich | 128/653.1 |
| 4,534,358 | 8/1985 | Young | 128/653 |
| 4,651,099 | 3/1987 | Vinegar et al. | 128/653.5 |
| 4,829,252 | 5/1989 | Kaufman | 324/309 |
| 4,875,485 | 10/1989 | Matsutani | 128/653.5 |
| 4,985,678 | 1/1991 | Gangaross et al. | 324/318 |
| 5,008,624 | 4/1991 | Yoshida | 324/318 |
| 5,207,224 | 5/1993 | Dickinson et al. | 128/653.5 |

FOREIGN PATENT DOCUMENTS 62-26052  2/1987  Japan .
2215522  9/1989  United Kingdom .

*Primary Examiner*—Ruth S. Smith
*Attorney, Agent, or Firm*—Nixon & Vanderhye

[57] ABSTRACT

Special patient handling apparatus and method retains increased accessibility advantages for open C-magnet MRI system architecture. The required volume for an accompanying RF shielded gantry room may also be minimized. The special patient transport mechanism may include a structure which at least partly telescopes around the lower pole face of the C-shaped MRI polarizing magnet as the patient is side-loaded into the image volume between the magnet pole faces. Substantially adjacent open accessibility to the patient is maintained throughout the loading procedure and throughout the subsequent preparatory and imaging procedures associated with the MRI system.

11 Claims, 7 Drawing Sheets

FIG. 2 (PRIOR ART)
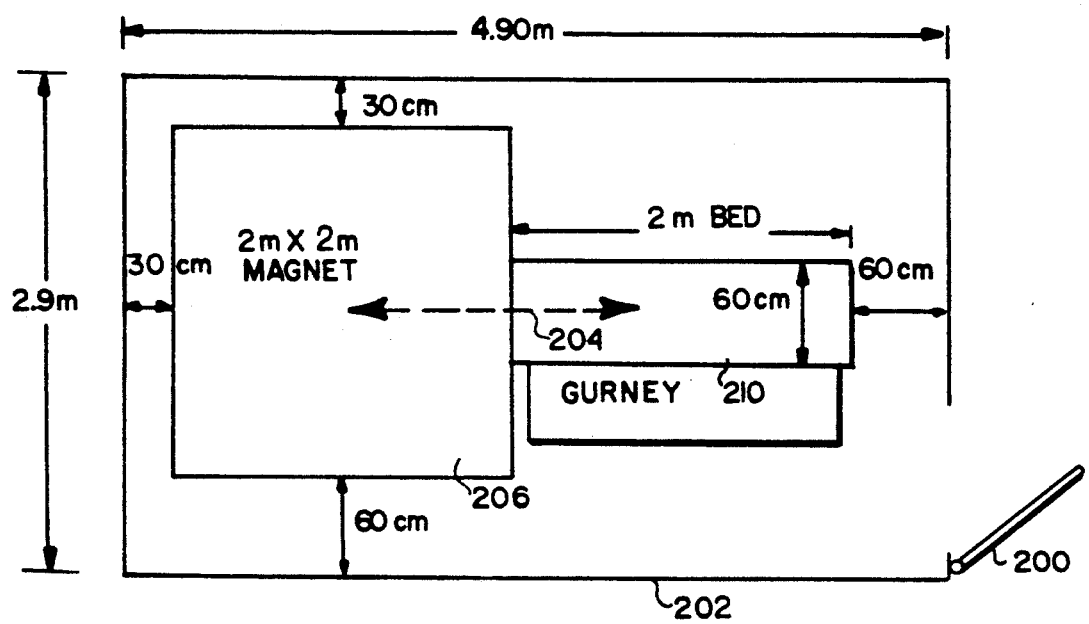
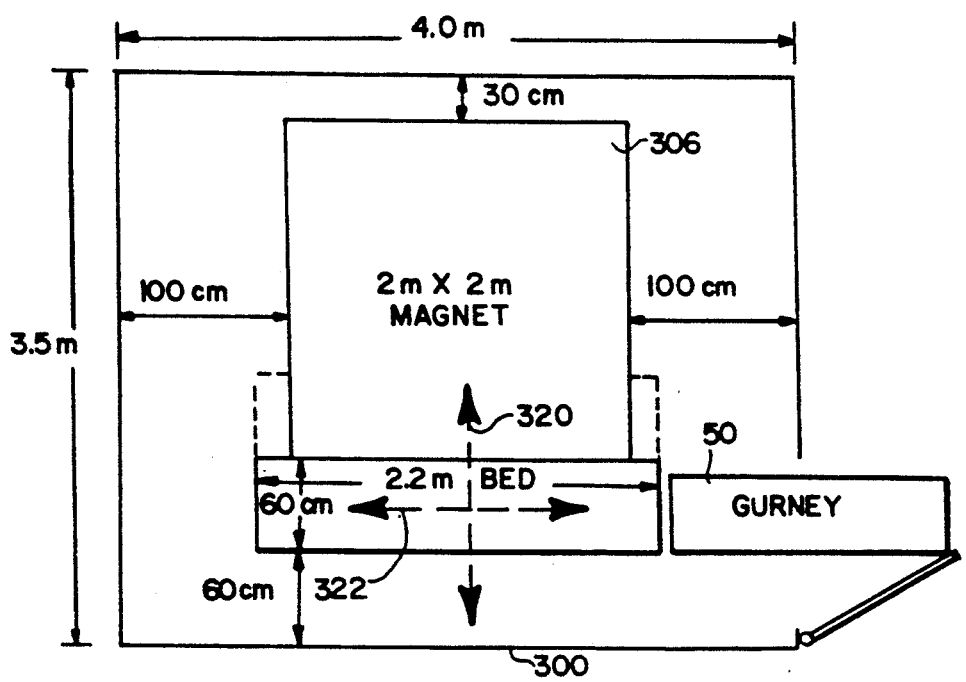
FIG. 3

SIDE-LOADING OF PATIENT INTO MRI C-MAGNET WHILE MAINTAINING ADJACENT OPEN ACCESSIBILITY TO PATIENT

BACKGROUND OF THE INVENTION

1. Field of the Invention

This invention relates to magnetic resonance imaging (MRI) utilizing nuclear magnetic resonance (NMR) phenomena. It is particularly directed to MRI systems and methods utilizing a C-shaped main polarizing magnet with opposing pole faces situated in approximately parallel horizontal planes above and below the image volume. Still more particularly, this invention is directed to method and apparatus for the transport of a patient into the image volume of such a C-shaped MRI magnet structure.

2. Related Art

MRI is now a well-known and commercially available technique for non-invasive imaging of patient tissue. Although there are many different species of MRI systems now available, all of them require a relatively massive polarizing magnet for producing a nominally static, nominally uniform NMR polarizing field within the volume to be imaged. Additional pulsed electromagnet gradient coils are utilized in conjunction with pulsed RF fields (via an RF antenna coil) to acquire raw MRI data (as NMR RF responses) during an imaging procedure. The raw data may be transformed into a visual image that represents the spatial distribution of NMR nuclei within the image volume (e.g., representing patient tissues) by a number of known procedures (e.g., via multiple Fourier Transformation).

One presently popular MRI system design utilizes a cryogenic solenoidal superconducting electromagnet to create the nominally static nominally uniform polarizing magnetic field. In such a design, the bore of the solenoid is of extended length and diameter so that the whole body of a patient may be transported completely within the bore during imaging procedures. This leaves essentially no access to the patient during preliminary procedures or during final imaging procedures. It also may provoke claustrophobic reactions in some patients and can interfere with the continuance of life support measures and the like which may be required by the patient. It further prevents almost any interventional procedures which attending medical personnel might wish to perform on the patient while in the image volume.

Another currently popular MRI system design utilizes permanent magnets in conjunction with substantially horizontal pole pieces that are opposingly disposed above and below the image volume. A return magnetic flux flows between the two poles via a plurality of vertical support members disposed at intervals (e.g., 90° intervals) around the periphery of the poles. This leaves substantially more open access to the image volume during preparatory and imaging procedures so as to permit interaction with the patient. It also tends to leave the patient in more of an "open" environment and thus lessens the likelihood of claustrophobic reactions. One such MRI system is described more particularly, for example, in commonly assigned U.S. Pat. No. 4,829,252 to Kaufman, the entire content of which is hereby incorporated by reference.

There have also been other approaches to a more "open" structure for the main polarizing magnet of a MRI system. Some examples are included in the following references (the entirety of each of which is hereby incorporated by reference):

U.S. Pat. No. 4,534,358—Young (1985)
U.S. Pat. No. 4,985,678—Gangarosa et al (1991)
U.S. Pat. No. 5,008,624—Yoshida (1991)
British GB 2,215,522A—McGinley (1989)
Japanese Patent Appln. 62-26052—Oikawa (1987)

With respect to side-loading patient transport mechanisms having relevance to this invention, the most pertinent of the above references is probably the Japanese application 62-26052 to Oikawa. Here, Oikawa does teach side-loading patient transport apparatus for use with a C-shaped main MRI polarizing magnet. However, Oikawa cantilevers the patient bed on a wide base pedestal which remains as a substantial obstruction between any attending personnel and the patient after the patient has been side-loaded into the image volume. Thus, although there is still some accessibility to the patient during preparatory and imaging procedures, the attending personnel would have to inconveniently lean over the wide base pedestal unit to reach the patient in the imaging volume. Accordingly, this prior approach still fails to provide advantageous substantially adjacent open accessibility to the patient.

SUMMARY OF THE INVENTION

This invention now provides a patient transport bed that can be movably telescoped over at least a portion of the lower pole face of a C-shaped NMR polarizing magnet while simultaneously retaining substantially unaltered adjacent open-accessibility to a patient disposed on the bed. In one example of the invention a movable patient transport has spaced-apart structures supporting a horizontal patient bed and an opening under the bed sized to pass the lower magnet pole therethrough while interjecting the patient bed into the gap so as to permit substantially adjacent patient access along a side of the patient while the patient is positioned within the MRI image volume.

The MRI system of this invention may include the polarizing magnet disposed within a conductively shielded gantry room and a movable patient transport including a plurality of depending legs on rollers for movement over an underlying surface into the gantry room and for straddling opposite side edges of the lower pole when the patient bed is moved into the gap. The movable transport may move the patient bed in at least two dimensions with respect to the spaced-apart structures.

Preferably the patient bed transport that is movable into the magnet by a transport undercarriage does not occupy any substantial space at the front edge of the gap after the bed is located within the gap.

The invention also includes a method for positioning a patient for MRI using an NMR polarizing magnet with a C-shaped cross-section. According to the invention, a patient is placed on a movable bed having an aperture in an undercarriage disposed below the bed; and the bed is then moved into juxta-position with the open gap of the C-shaped magnet. The bed is moved into the open gap while moving the aperture therebelow over a lower pole face of the magnet thus leaving unobstructed adjacent access to the patient along an entire patient body side while the patient is disposed within said gap. Preferably, the bed position is adjusted within the gap along at least two dimensions with respect to the undercarriage after the bed has been located within the gap and the undercarriage has been positioned over the lower pole face.

BRIEF DESCRIPTION OF THE DRAWINGS

These as well as other novel advantages and features of this invention will become more clearly apparent upon careful study of the following detailed description of presently preferred exemplary embodiments of this invention in conjunction with accompanying drawings, of which:

FIG. 2 is a schematic plan depiction of a typical prior art RF-screened gantry room arrangement;

FIG. 3 is a similar schematic plan view of a differently configured and slightly smaller RF-screened gantry room that might be used with this invention;

DETAILED DESCRIPTION OF EXEMPLARY EMBODIMENTS

Figure 1:
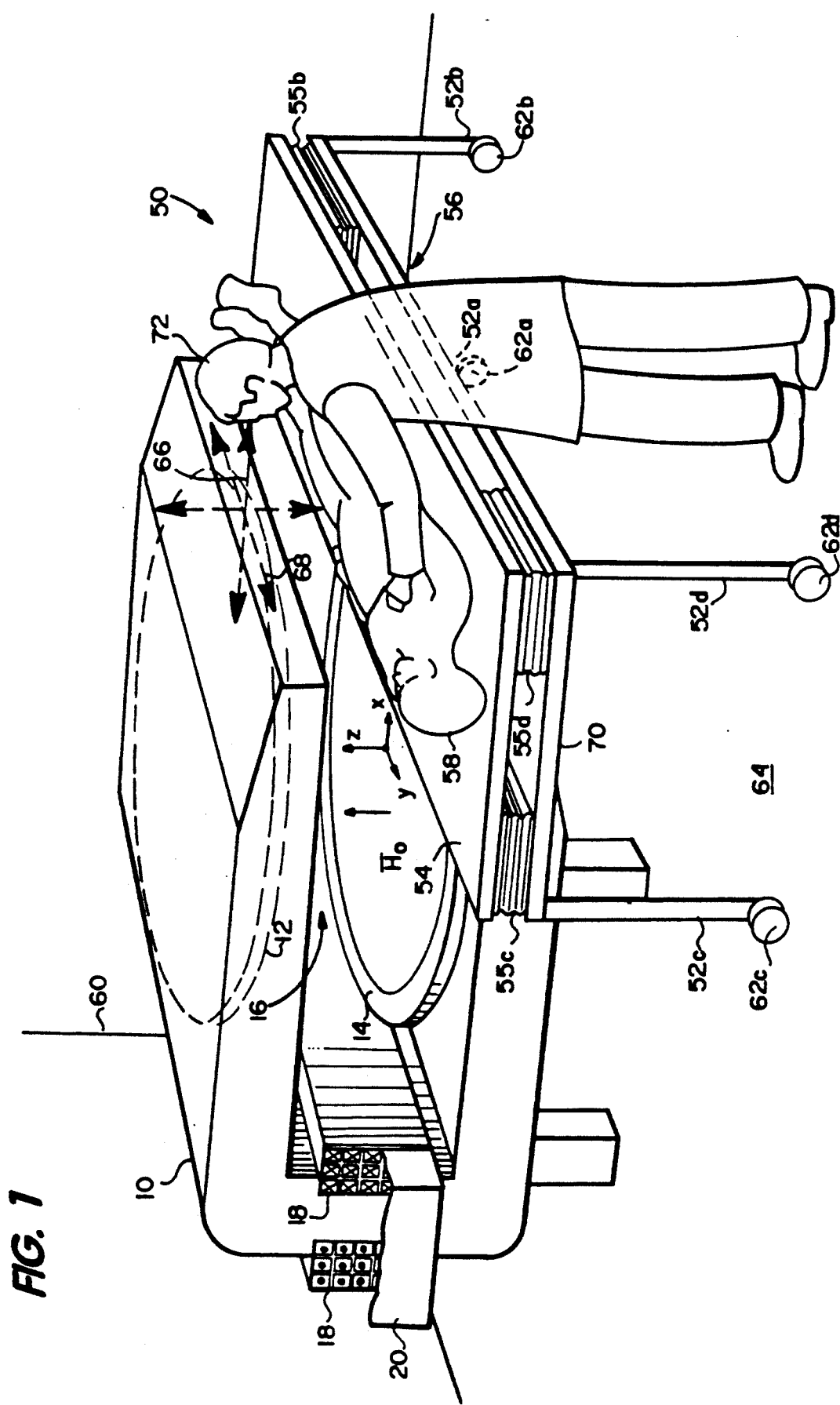
FIG. 1 is a perspective view of a first embodiment of this invention schematically depicting a patient in the process of being side-loaded into a C-shaped MRI magnet imaging volume semiconductor.

As depicted in FIG. 1, this invention is designed for use with a C-shaped NMR polarizing magnet 10. C-shaped magnets for use in MRI have already been proposed (e.g., see above noted citations). They typically may include a magnetically permeable core (e.g., various known forms of "iron") having the characteristic "C" shape in cross-section. Pole faces 12, 14 typically including annular "Rose" shims and "pancake" flat gradient coils (as explained in U.S. Pat. No. 4,829,252) may be provided at each terminus of the C-shaped magnetically permeable yoke so as to define a substantially uniform NMR polarizing magnetic field $H_o$ within an image volume 16 disposed within the gap defined between the two pole faces 12, 14. As can be seen in FIG. 1, the gap is unobstructed at three sides (e.g., the "front" and opposing "end" sides).

The C-shaped magnet 10 can be driven by permanent magnets (e.g., incorporated within the pole structures 12, 14) or by resistive or superconducting electromagnet windings. For example, superconducting windings 18 (shown in rectangular cross-section with current directions depicted out of and into the drawing plane in accordance with the usual conventions) may be disposed within a single cryostat 20 that is symmetrically disposed about the central portion of the C-shaped magnet 10. Reducing the number of cryostats to a single cryostat is of great economic advantage. As it turns out, location of the single cryostat in a symmetric position as depicted in FIG. 1 appears preferable to locating it elsewhere along the magnetic circuit (e.g., about one of the pole pieces 12, 14). This is so, at least in part, because it tends to make the magnetic field more symmetric in the z-axis dimension.

For various reasons, many manufacturers of MRI systems have designed the outer covers so as to result in a relatively long cylindrical bore (of circular or square cross-section) through which the patient must be inserted into the imaging volume. This was initially the case in instances even when the magnet structure itself is of more open architecture. However, as pointed out more completely in U.S. Pat. No. 4,829,252 (Kaufman, issued May 9, 1989 and commonly assigned herewith) such designs adversely restrict patient accessibility during preparatory and imaging procedures. Open patient accessibility is a very desirable quality for, among other things, patient comfort, patient handling and interventional procedures. It now appears that more and more consideration is being given to C-shaped polarizing magnet designs that provide essentially completely open accessibility from three sides of the image volume. This may be thought of, for example, as an extension of the four-post return magnetic flux circuit as depicted in the Kaufman '252 patent by moving two of the posts to the other side (thus closing off one side entirely and cantilevering the top most pole piece while leaving completely unobstructed the three other sides of the magnet structure).

While Oikawa has already recognized that there may be advantages to side-loading of a patient into the patient image volume using C-shaped NMR polarizing magnets, these earlier side-loading attempts use a substantial base pedestal that remains as an obstruction between attending personnel and the patient once the patient has been side-loaded into the image volume between the magnet pole faces.

As depicted in the exemplary embodiment of this invention shown in FIG. 1, the moveable patient transport 50 has spaced-apart legs 52A, 52B, 52C and 52D which support the horizontal patient bed 54 while leaving an opening 56 under the bed sized so as to pass the lower magnet pole 14 therethrough while interjecting the patient bed 54 laterally into the gap and patient image volume 16. In this manner, adjacent patient access is constantly maintained along an entire side of the patient 58 while the patient is being positioned within the MRI image volume 16.

In the exemplary embodiment of FIG. 1, the polarizing magnet 10 is disposed within a conductively shielded gantry room 60 while the depending legs 52A-52D are supported on rollers 62A, 62B, 62C and 62D for movement over the underlying floor surface 64 of the room while straddling opposite side edges of the lower pole structure 14 when the patient bed 54 is moved into the gap area. As depicted in FIG. 1, the patient bed 54 is preferably mounted on multi-dimensional movement modules 55a (not shown but located below the remaining corner of bed 54) 55b, 55c and 55d. Although motorized controls may be used, conventional hand operated movement mechanisms should suffice. For example, existing bed support systems provide for manual movements in two dimensions using roller and brake mechanisms. Vertical movement linkages are also conventionally available. For example, translational movements may be made along x and y axes (as schematically depicted by arrows 66 and 68, respectively) with respect to the underlying patient transport structure 70 (which is in this exemplary embodiment fixedly secured with respect to the depending legs 52a–d). In addition, the patient bed 54 is preferably adapted for translational movements in the third direction (e.g., along the z-axis) as well so as to provide complete three-dimensional positioning freedom of the patient anatomy with respect to the image volume. For example, the patient transport 50 may be laterally moved to telescope over the lower underlying pole face 14. The substructure even may be latchably affixed with respect to the magnet 10 if desired. Thereafter, any desired further relative movement in x,y,z directions of the patient bed 54 may be made with respect to the image volume 16 so as to exactly position the patient as desired for imaging procedures.

Of course, as will be well understood by those in the art, the materials used for the patient transport 50 must be compatible with the high-strength magnetic field environment to be encountered within the gantry room 60.

Although it is conceivable that there might be some relatively thin structure present along the front of the transport undercarriage 70, it should not occupy any substantial space at the front edge of the gap after the bed is located within the gap. That is, the attending personnel 72 should remain substantially adjacent the patient 58 even after the patient transport structure 50 has been positioned so as to place the patient within the image volume 16. In this manner, substantially adjacent open accessibility to the patient 50 is maintained at all times.

As will be appreciated in view of the foregoing description, this invention also includes a novel method for positioning a patient for MRI using an NMR polarizing magnet with a C-shaped cross-section. In this new method, the patient is first placed on a moveable bed 54 on an undercarriage 70 having an aperture 56 therein disposed below the bed. Thereafter, the bed is moved into juxtaposition with the open gap and image volume 16 of C-shaped magnet. Finally, the bed 54 is moved into the open gap and image volume 16 while moving the aperture 56 over the lower pole face 14 of the magnet thus leaving unobstructed adjacent access to the patient along an entire patient body side while the patient is disposed within the image volume 16. Furthermore, the patient bed 54 may be adjusted in three dimensions with respect to the undercarriage 70 after the bed has been located within the image volume 16 and the undercarriage has been positioned over the lower pole face 14.

As will be appreciated, the patient generally has a shorter distance to travel into the unit by this side-loading procedure. Especially, when the patient transport mechanism 50 itself telescopes over a portion of the magnet structure, one can achieve important economies in patient transport which relate to the necessary size of an expensive RF-shielded gantry room.

For example, a typical prior art system is schematically depicted in plan view at FIG. 2. Here, the patient gurney passes through door 200 of screened room 202. The gurney is then positioned with the patient's longitudinal axis aligned for movement as indicated by arrow 204 along suitable patient transport tracking into the patient image volume within magnet 206. Typically the patient transport mechanism 210 includes an undercarriage which remains wholly outside the magnet structure even after the patient has been moved along axis 204 into the image volume. Approximately minimum dimensions for the gantry room are shown in FIG. 2 for such a prior art arrangement so as to result in approximate plan area of 14.2 square meters.

Figure 4:
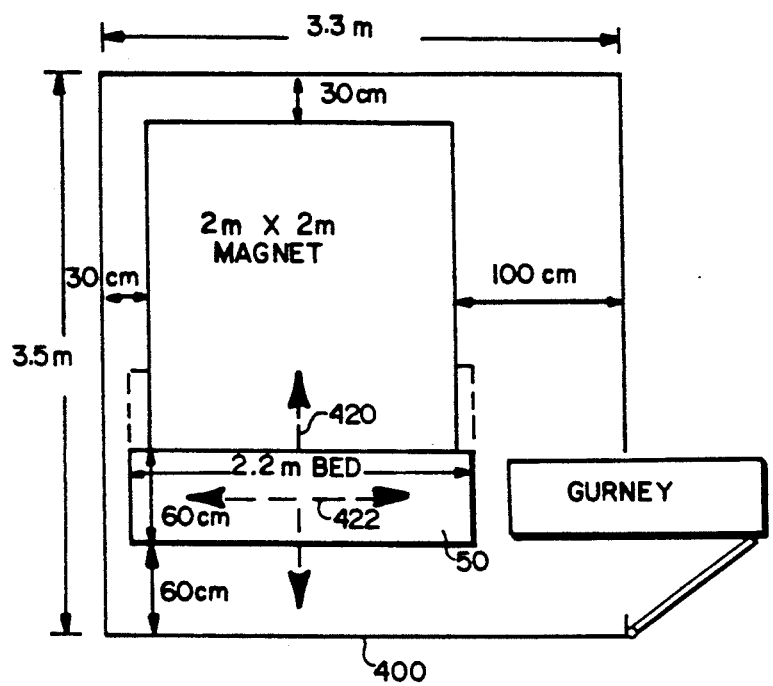
FIG. 4 is yet another schematic plan view of an RF-screened gantry room having considerably smaller dimensions and which may be suitable for use with this invention.

As shown in FIG. 3, even if approximately the same plan area (e.g., 14 square meters) is maintained for RF screen room 300 utilizing the side-loading gurney of this invention, there is substantially more access room provided around the three open sides of magnet 306 within the gantry room—both before and after the patient transport 50 has been moved laterally along line 320 into telescoping relationship with the lower pole of magnet 306. As also depicted by arrow 322 in FIG. 3 (and as earlier described), once inside the magnet 306, the patient organ of interest can be centered within the image volume by displacing the bed along the patient axis as depicted by arrow 322. If, as in conventional systems (e.g., as shown in FIG. 2), care is taken to place the patient's head or feet first so as to minimize the need for space on the backside of the magnet, then travel can be restricted to essentially one direction 422 as depicted in FIG. 4 after the patient transport 50 has been laterally moved along line 420 into the patient volume. The area of the RF-shielded gantry room for this latter configuration (FIG. 4) can thus be substantially reduced in area (e.g., to 11.6 square meters or approximately 20%) while still retaining ample working space around the magnet and bed. Although the plan views of FIGS. 3 and 4 have maintained substantial access room to the patient even before the patient is inserted into the magnet structure, it will be appreciated that since patient access is still unrestricted even after the patient is inserted into the magnet structure, one might further reduce the area of the RF-shielded gantry room by reducing available access space to the patient prior to such lateral movement of the patient transport into the magnet structure.

A C-shaped NMR polarizing magnet using a resistive electromagnet already exists. At least a scale model of a C-shaped permanent magnet has also been built (e.g., by Sumitomo). C-shaped supercon electromagnet designs are also believed feasible. For example, in the cross-sectional depiction of magnet 10 depicted at FIG. 5, a central field strength of approximately 0.35 Tesla is desired. Assuming that an average wire current in the superconducting wires 20 is 5 KA/cm$^2$ and that 100 KA is needed for a particular design, then approximately 20 cm$^2$ of superconductor is needed. Further assuming that the insulation gap is approximately 10 centimeters on each side, then the cryostat 20 might be approximately 22 by 30 centimeters in dimension. Other possible overall dimensions in terms of centimeters are given in the scales included at FIG. 6A, 6B, 7A and 7B.

Figure 5:
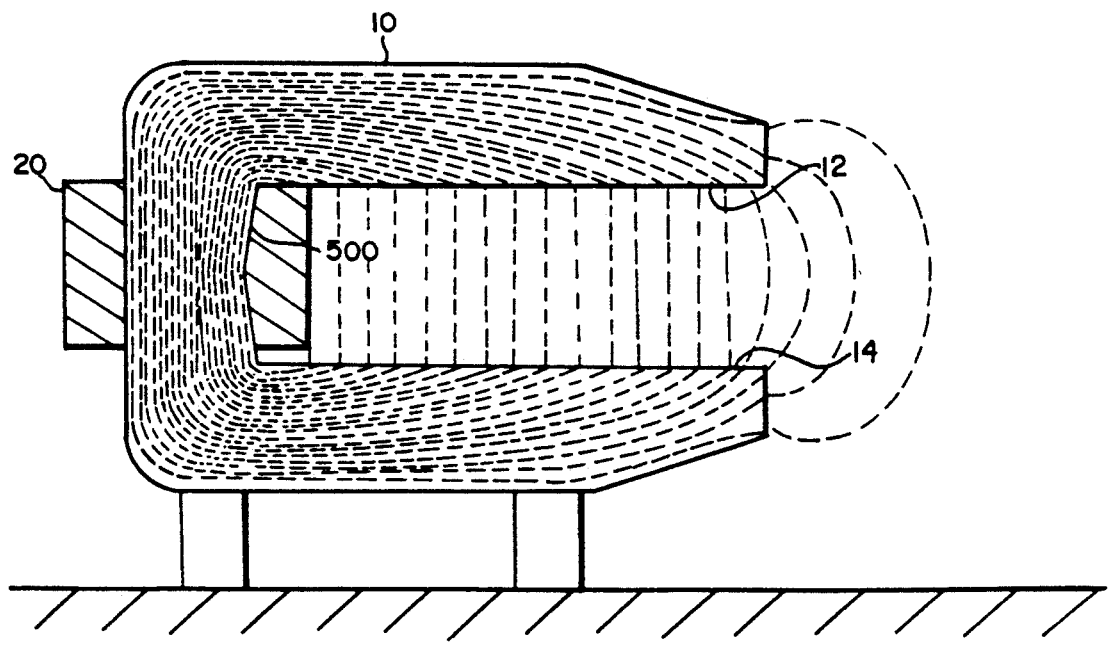
FIG. 5 is a schematic cross-sectional view of a C-shaped MRI polarizing magnet including shimming features that may be useful with this invention.

In addition, the exemplary embodiment of FIG. 5 utilizes at least two main shimming features. First of all, horizontal inhomogeneity is reduced by making the pole places slightly tilted from horizontal. In the example of FIG. 5, the upper pole face 12 would tilt downwardly slightly toward the open front and the lower pole face 14 would tilt upwardly slightly toward the open front. In one possible design, the angle of such tilt may have a tangent of approximately 0.001. Secondly, to reduce vertical field inhomogeneities, the central post wall is symmetrically tilted toward the front of the magnet (in each direction from the mid-point) as depicted at 500 in FIG. 5. In one potential exemplary embodiment, the tangent of such tilt angle of the post wall is approximately 0.1666667.

A two-dimensional computer simulation for the design of FIG. 5 produces the following results:
Central Field: 3,500 Gauss
Current: 176,000 Amps
Poleface Diameter: 180 cm
Gap: 60 cm
Length: 180 cm
Width: 240 cm
Height: 140 cm
Weight: 45,000–55,000 lbs
5 Gauss line radius: 800 cm
Coil loop length: 360–430 cm
Field inhomogeneity: 56 PPM(2 D simulation)

Figure 6A:
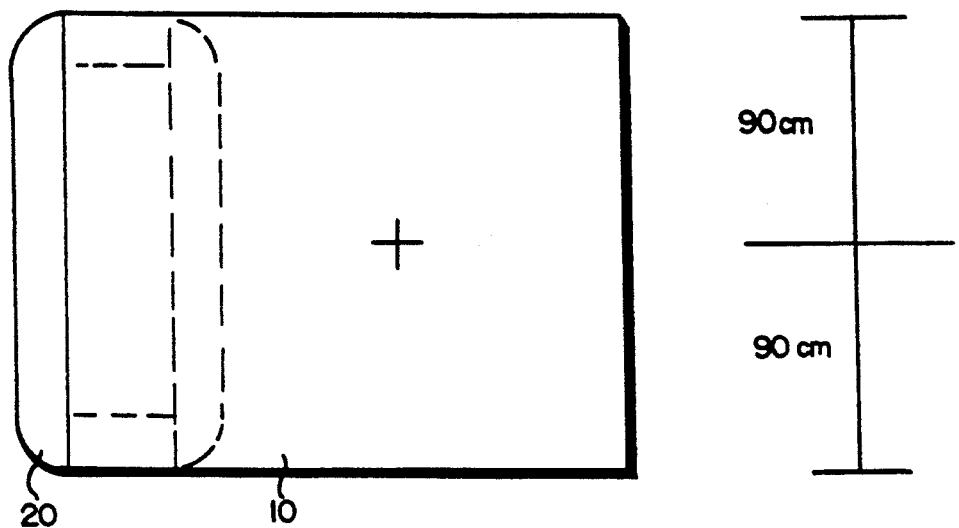
FIGS. 6A and 6B are schematic plan and side-views, respectively, of a C-shaped MRI polarizing magnet that may be used for this invention.
Figure 6B:
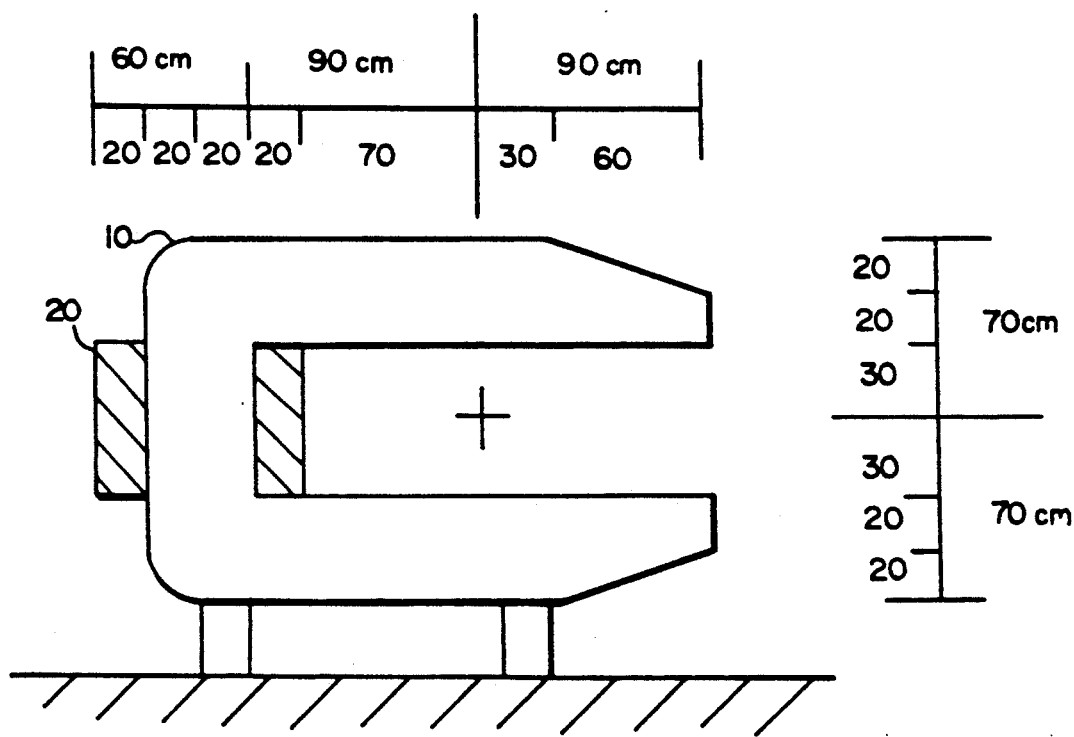
Figure 7A:
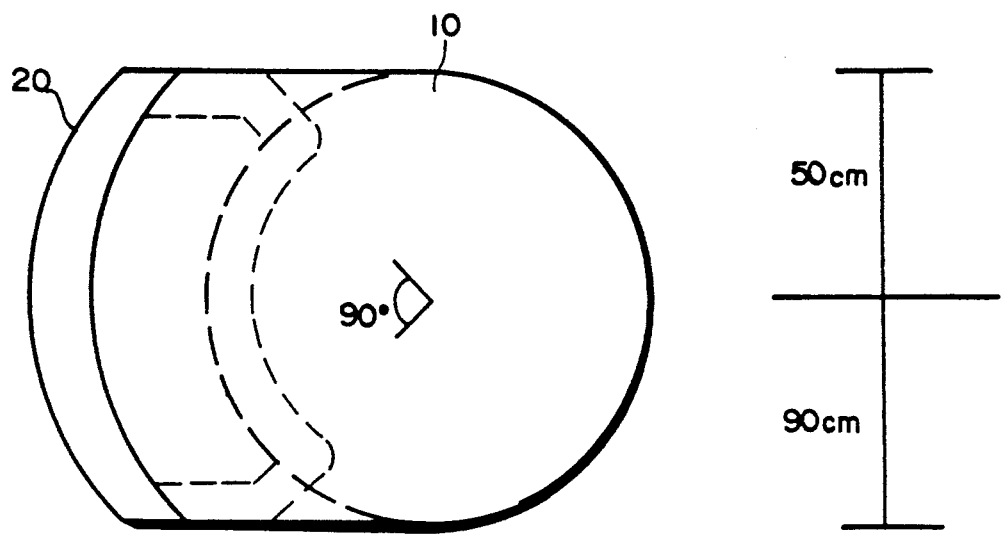
FIGS. 7A and 7B are similar schematic plan and side-views of a slightly different C-shaped MRI magnet design that may be used with this invention.
Figure 7B:
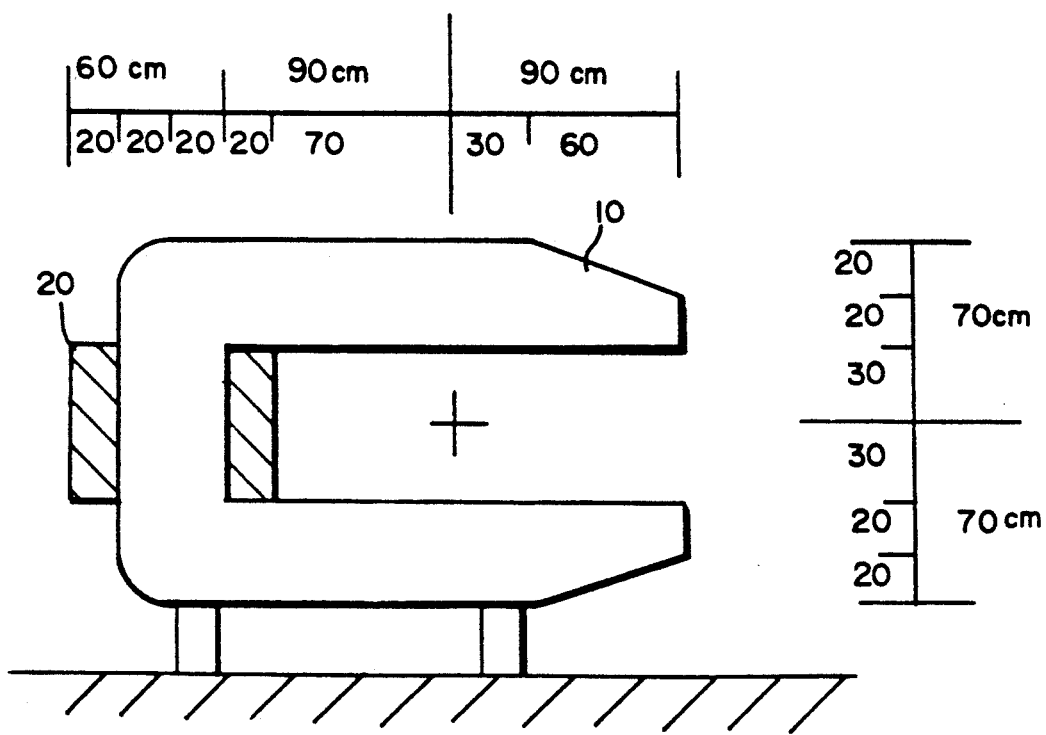

The design of FIG. 5 may have a square-edged plan shape as depicted in FIG. 6A or a round-edged plan shape as depicted in FIG. 7A. While there may be a considerable savings in weight for FIG. 7A versus FIG. 6A (e.g., a weight savings of as much as 10,000 pounds), there may be need for an increased coil loop length of the superconducting wire in cryostat 20 for the FIG. 7A embodiment versus FIG. 6A embodiment (e.g., a coil loop length of approximately 430 centimeters may be required for FIG. 7A while only 360 centimeters may be required for at least some turns in FIG. 6A).

Of course it will be realized by those in the art that other types of completely open-sided NMR polarizing magnet structures may be used with this invention. Furthermore, those in the art will recognize that many techniques may be used for optimizing magnet shape so as to better reduce inhomogeneities in the image volume, to reduce fringe fields, to reduce the overall weight, to reduce needed cryogen and superconducting material, etc.

Figure 8A:
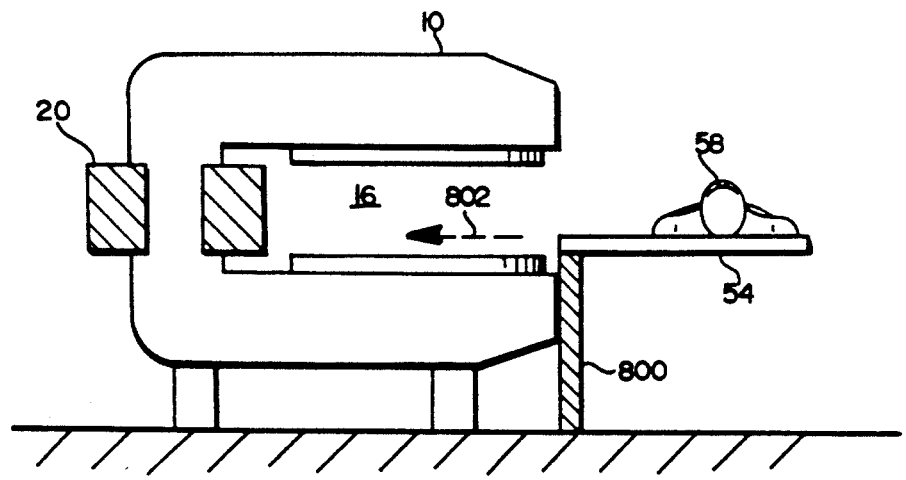
FIGS. 8A, 8B, 8C, 8D and 8E schematically depict alternate embodiments of this invention which might be used while still providing substantially adjacent open accessibility to the patient during preparatory or imaging procedures.
Figure 8B:
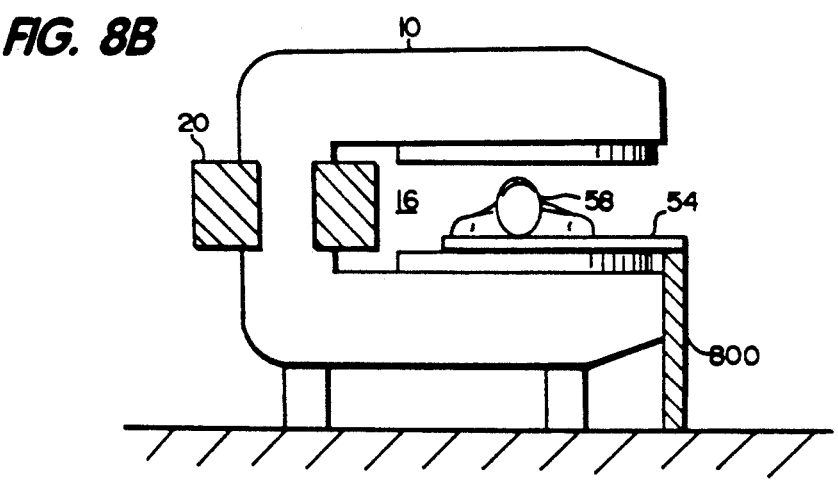

Although the presently preferred exemplary embodiment of FIG. 1 substantially telescopes the lower magnet base 14 within aperture 56 so as to leave a totally unobstructed access to the patient, it may be possible to provide other sorts of mechanical structures that would provide only the very minimum, if any, structure remaining between the attending personnel 72 and the patient 58 after positioning within the image volume 16. For example, as depicted in FIGS. 8A and 8B, if a minimal width support structure 800 is suitably supported (e.g., by structure disposed at the ends thereof and/or by physical attachment to the lower arm of magnet 10), then bed 54 may be slidably cantilevered thereon. Thus, the bed 54 might be positioned opposite the image volume 16 as depicted in FIG. 8A and then moved in the direction of arrow 802 so as to result in patient positioning within the image volume as depicted at FIG. 8B (where the bed 54 is now cantilevered on the opposite side of support structure 800). As may be appreciated, although there is some structure 800 between the lower arm of magnet 10 and attending personnel, there is no substantial obstruction and there is in fact still substantially adjacent open accessibility to the patient all along one side of the structure.

Figure 8C:
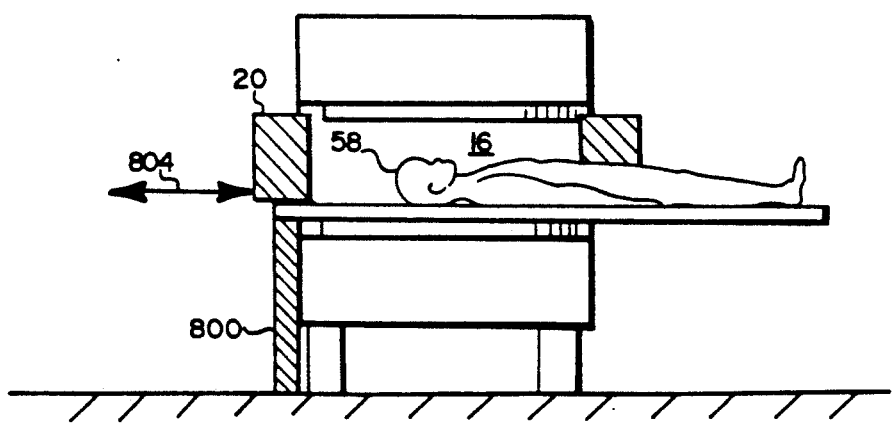

It is conceivable that other similar support structures such as 800' shown in FIG. 8C could be supported suitably (e.g., first by structure that permits transport along the floor and then by attachment to the massive magnet structure 10) while the patient bed 54 is slidably cantilevered thereon so that it may be moved along the line indicated by arrow 804 to place the patient into the image volume 16.

Figure 8D:
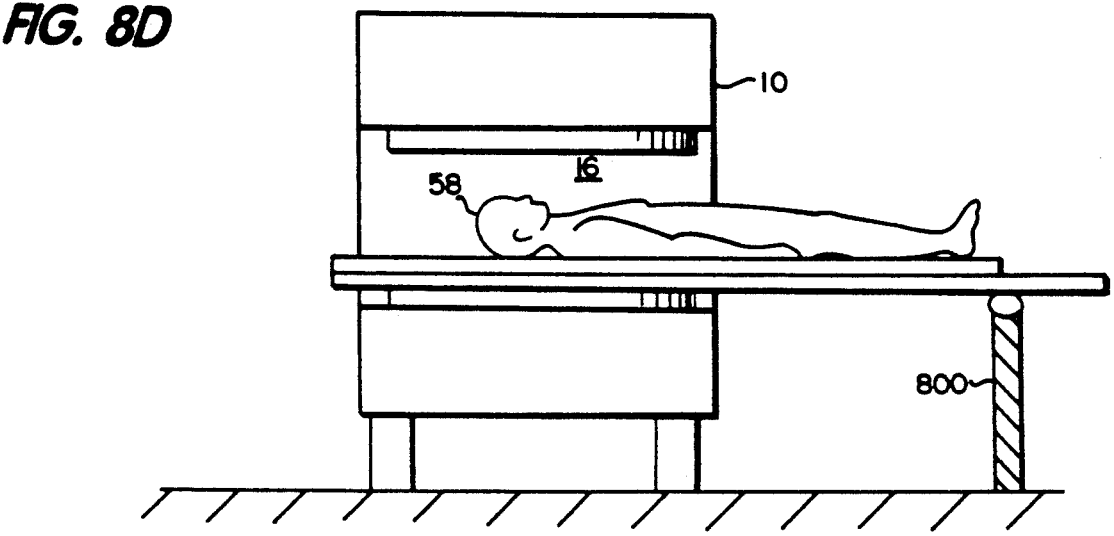
Figure 8E:
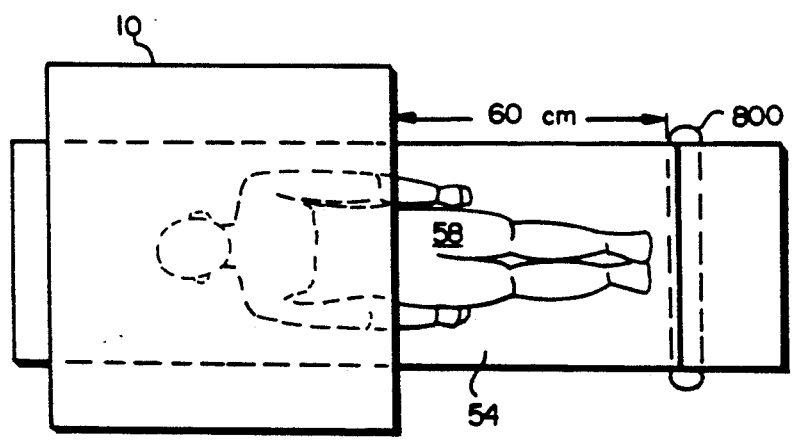

FIGS. 8D and 8E (in schematic elevation and plan views respectively) depict one possible arrangement where a fixed upright support 800 is spaced away from the magnet so as not to interfere with access to the patient. As can be seen, the embodiment of FIGS. 8D and 8E is similar to that of FIG. 8C in that the patient is moved along the longitudinal axis. However, in the embodiment of FIGS. 8D and 8E, the fixed support 800 has a roller support at its top to help support the bed at a point spaced away from the magnet as it is moved into and out of the magnet 10.

While only a few exemplary embodiments of this invention have been described in detail, those skilled in the art will recognize that it is possible to make many modifications and variations in these embodiments while yet retaining novel features and advantages of this invention. Accordingly, all such variations and modifications are intended to be included within the scope of the appended claims.

What is claimed is:

1. In an MRI system including a C-shaped NMR polarizing magnet having an MRI image volume in a gap between upper and lower pole faces thereof, the improvement comprising,
   a patient transport bed movably mounted to an undercarriage having a plurality of depending legs on rollers, said undercarriage including an aperture sized for telescopic movement over at least a portion of the lower pole face while simultaneously retaining substantially unaltered adjacent open-accessibility to a patient disposed on the bed.

2. In an MRI system including an NMR polarizing magnet having opposed upper and lower horizontal poles defining a MRI image volume within a gap between the poles that is open about at least three sides, the improvement comprising:
   a movable patient transport having spaced-apart structures supporting a horizontal patient bed and depending therefrom and defining an opening under the bed sized to pass said lower magnet pole therethrough while interjecting the patient bed into said gap so as to permit substantially adjacent patient access along a side of the patient while the patient is positioned within the MRI image volume.

3. A MRI system as in claim 2 wherein said polarizing magnet is disposed within a conductively shielded gantry room and said movable patient transport comprises:
   a plurality of depending legs on rollers for movement over an underlying surface into said gantry room and for straddling opposite side edges of said lower pole when the patient bed is moved into the gap.

4. A MRI system as in claim 3 wherein said movable patient transport comprises:
   means for moving the patient bed in at least two dimensions with respect to said spaced-part structures.

5. A MRI system as in claim 2 wherein said movable patient transport comprises:
   means for moving the patient bed in at least two dimensions with respect to said spaced-apart structures.

6. In an MRI system including an NMR polarizing magnetic circuit having a C-shaped cross-section of magnetically permeable material with pole faces at each terminus thereof to define a substantially uniform NMR polarizing magnetic field in an image volume within the gap between the two pole faces, said gap being unobstructed at its front and opposing end edges, the improvement comprising:
   a patient bed mounted on a transport undercarriage having a plurality of depending legs that are disposed for movement on a floor surface and for movement into said gap said transport undercarriage not occupying any substantial space at the front edge of said gap after the bed is located within the gap.

7. A MRI system as in claim 6 wherein said polarizing magnet is disposed within a conductively shielded gantry room and wherein:
said plurality of depending legs are mounted on rollers for movement over an underlying surface into said gantry room and for straddling opposite side edges of said lower pole when the patient bed is moved into the gap.

8. A MRI system as in claim 7 wherein said movable patient bed transport comprises:
means for moving the patient bed in at least two dimensions with respect to said depending legs.

9. A MRI system as in claim 6 wherein said movable patient transport comprises:
means for moving the patient bed in at least two dimensions with respect to said gap.

10. A method for positioning a patient for MRI using an NMR polarizing magnet with a C-shaped cross-section, said method comprising:
placing said patient on a movable bed having an aperture in an undercarriage disposed below the bed;
moving said bed into juxta-position with the open gap of the C-shaped magnet; and
moving said bed into said open gap while moving said aperture therebelow over a lower pole face of the magnet thus leaving unobstructed adjacent access to the patient along an entire patient body side while the patient is disposed within said gap.

11. A method as in claim 10 further comprising:
further adjusting the bed position within the gap along at least two dimensions with respect to said undercarriage after the bed has been located within the gap and the undercarriage has been positioned over the lower pole face.

* * * * *

REEXAMINATION CERTIFICATE (4069th)

United States Patent [19]
Li et al.

[11] B1 5,305,749
[45] Certificate Issued May 2, 2000

[54] SIDE-LOADING OF PATIENT INTO MRI C-MAGNET WHILE MAINTAINING ADJACENT OPEN ACCESSIBILITY TO PATIENT

[75] Inventors: Andrew J. Li, South San Francisco; Leon Kaufman, San Francisco, both of Calif.

[73] Assignee: The Regents of the University of California, Oakland, Calif.

Reexamination Request:
No. 90/005,017, Jun. 16, 1998

Reexamination Certificate for:
Patent No.: 5,305,749
Issued: Apr. 26, 1994
Appl. No.: 08/950,277
Filed: Sep. 24, 1992

[51] Int. Cl.[7] .................................................. A61B 5/055
[52] U.S. Cl. ............................... 600/415; 5/601; 324/318
[58] Field of Search .................................... 600/410, 415, 600/407; 5/600, 601; 324/318, 322

[56] References Cited

U.S. PATENT DOCUMENTS

| | | |
|---|---|---|
| Re. 29,888 | 1/1979 | Kaplan . |
| 4,131,802 | 12/1978 | Braden et al. . |
| 4,230,129 | 10/1980 | LeVeen . |
| 4,407,292 | 10/1983 | Edrich . |
| 4,534,358 | 8/1985 | Young . |
| 4,567,894 | 2/1986 | Bergman . |
| 4,651,099 | 3/1987 | Vinegar et al. . |
| 4,681,308 | 7/1987 | Rice . |
| 4,727,328 | 2/1988 | Carper et al. . |
| 4,771,785 | 9/1988 | Duer . |
| 4,777,464 | 10/1988 | Takabatashi et al. . |
| 4,805,626 | 2/1989 | DiMassimo et al. . |
| 4,829,252 | 5/1989 | Kaufman . |
| 4,862,086 | 8/1989 | Maeda . |
| 4,875,485 | 10/1989 | Matsutani . |
| 4,960,106 | 10/1990 | Kubokawa et al. . |
| 4,985,678 | 1/1991 | Gangarosa et al. . |
| 5,008,624 | 4/1991 | Yoshida . |
| 5,207,224 | 5/1993 | Dickinson et al. . |

FOREIGN PATENT DOCUMENTS

| | | |
|---|---|---|
| 187389A3 | 7/1986 | European Pat. Off. . |
| 314262A2 | 5/1989 | European Pat. Off. . |
| 3639140 A1 | 5/1987 | Germany . |
| 61-114148A | 5/1986 | Japan . |
| 62-26052 | 2/1987 | Japan . |

OTHER PUBLICATIONS

Diagnostic Imaging, The Newsmagazine of Radiology Nuclear Medicine and Ultrasound, Jun. 1984.

*Primary Examiner*—Brian Casler

[57] ABSTRACT

Special patient handling apparatus and method retains increased accessibility advantages for open C-magnet MRI system architecture. The required volume for an accompanying RF shielded gantry room may also be minimized. The special patient transport mechanism may include a structure which at least partly telescopes around the lower pole face of the C-shaped MRI polarizing magnet as the patient is side-loaded into the image volume between the magnet pole faces. Substantially adjacent open accessibility to the patient is maintained throughout the loading procedure and throughout the subsequent preparatory and imaging procedures associated with the MRI system.

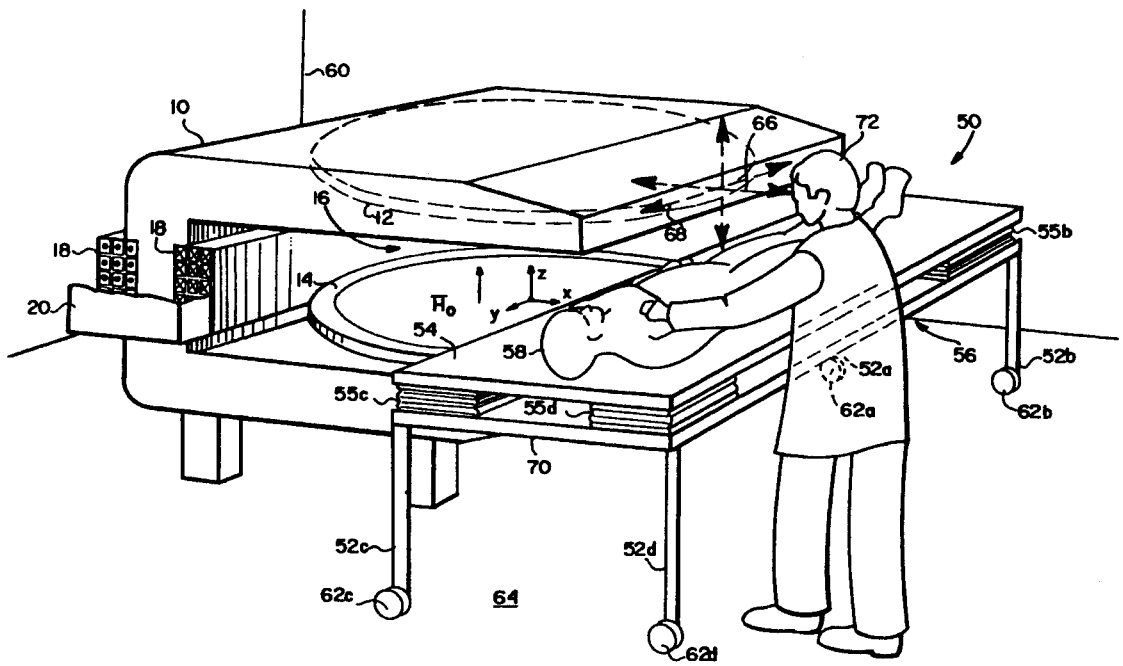

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1–6, 8, and 10 are determined to be patentable as amended.

Claims 7, 9, and 11, dependent on an amended claim, are determined to be patentable.

New claims 12 and 13 are added and determined to be patentable.

1. In an MRI system including a C-shaped NMR polarizing magnet having an MRI image volume in a gap between upper and lower pole faces thereof, the improvement comprising,
a patient transport bed movably mounted to an undercarriage having a plurality of depending legs on rollers, said undercarriage including an aperture sized for telescopic movement over at least a portion of the lower pole face while simultaneously retaining substantially unaltered adjacent open-accessibility to a patient disposed on the bed,
*said patient transport bed having a first position separated from the C-shaped NMR polarizing magnet, and at said first position the rollers are enabled to allow movement of the undercarriage with respect to the lower pole face of the NMR polarizing magnet; and*
*said patient transport bed having a second position within the gap, and at said second position the undercarriage is telescoped over the lower pole face and the rollers are disabled to prevent movement of the undercarriage with respect to the lower pole face.*

2. In an MRI system including an NMR polarizing magnet having opposed upper and lower horizontal poles defining a MRI image volume within a gap between the poles that is open about at least three sides, the improvement comprising:
a movable patient transport having spaced-apart structures supporting a horizontal patient bed and depending therefrom, and defining an opening under the bed sized to pass said lower magnet pole therethrough while interjecting the patient bed into said gap so as to permit substantially adjacent patient access along a side of the patient while the patient is positioned within the MRI image volume,
*said patient transport having a first position separated from the NMR polarizing magnet, and at said first position the movable patient transport is enabled to allow movement of the bed and the spaced-apart structures, and*
*said patient transport having a second position in the gap, and at said second position the spaced-apart structures of the transport bed are telescoped over the lower magnet pole and the spaced-apart structures are latched to prevent movement with respect to said lower magnet pole.*

3. A MRI system as in claim 2 wherein said polarizing magnet is disposed within a conductively shielded gantry room and said *spaced-apart structures of said* movable patient transport [comprises] *comprise*:
a plurality of depending legs on rollers for movement over an underlying surface into said gantry room and for straddling opposite side edges of said lower pole when the patient bed is moved into the gap.

4. A MRI system as in claim 3 wherein said movable patient transport comprises:
means for moving the patient bed in at least two dimensions with respect to said [spaced-part] *spaced-apart* structures, *while said patient transport is in said second position.*

5. A MRI system as in claim 2 wherein said movable patient transport comprises:
means for moving the patient bed in at least two dimensions with respect to said spaced-apart structures, *while said patient transport is in said second position.*

6. In an MRI system including an NMR polarizing magnetic circuit having a C-shaped cross-section of magnetically permable material with pole faces at each terminus thereof to define a substantially uniform NMR polarizing magnetic field in an image volume within the gap between the two pole faces, said gap being unobstructed at its front and opposing end edges, the improvement comprising:
a patient bed mounted on a transport undercarriage having a plurality of depending legs that are disposed for movement on a floor surface and for movement into said gap said transport undercarriage not occupying any substantial space at the front edge of said gap after the bed is located within the gap;
*said patient bed and said transport undercarriage having a first position separated from the NMR polarizing magentic, and at said first position the transport undercarriage is enabled to allow movement of the undercarriage across the floor surface, and*
*said patient bed and said transport undercarriage having a second position where the bed is in the gap and the undercarriage is telescoped over said lower magnet pole, and where the undercarriage is latchably affixed to prevent movement of the undercarriage with respect to the lower magnet pole.*

8. A MRI system as in claim 7 wherein said movable patient [bed] transport comprises:
means for moving the patient bed in at least two dimensions with respect to said depending legs.

10. A method for positioning a patient for MRI using an NMR polarizing magnet with a C-shaped cross-section, said method comprising:
placing said patient on a movable bed having an aperture in an undercarriage disposed below the bed, *while said bed is separated from the NMR polarizing magnet*;
moving said bed *and undercarriage* across a floor towards said NMR polarizing magnet and into juxta-position with the open gap of the C-shaped magnet; and
moving said bed into said open gap while moving said aperture therebelow over a lower pole face of the magnet thus leaving unobstructed adjacent access to the patient along an entire patient body side while the patient is disposed within said gap.

12. An MRI system as in claim 2 wherein said the patient bed moves in at least two dimensions with respect to the spaced-apart structures, while said bed and the spaced-apart structures are in the second position.

13. An MRI system as in claim 2 wherein said the patient bed moves in at least two dimensions with respect to the spaced-apart structures, while said bed and the spaced-apart structures are in the second position.

* * * * *